Figure 1:
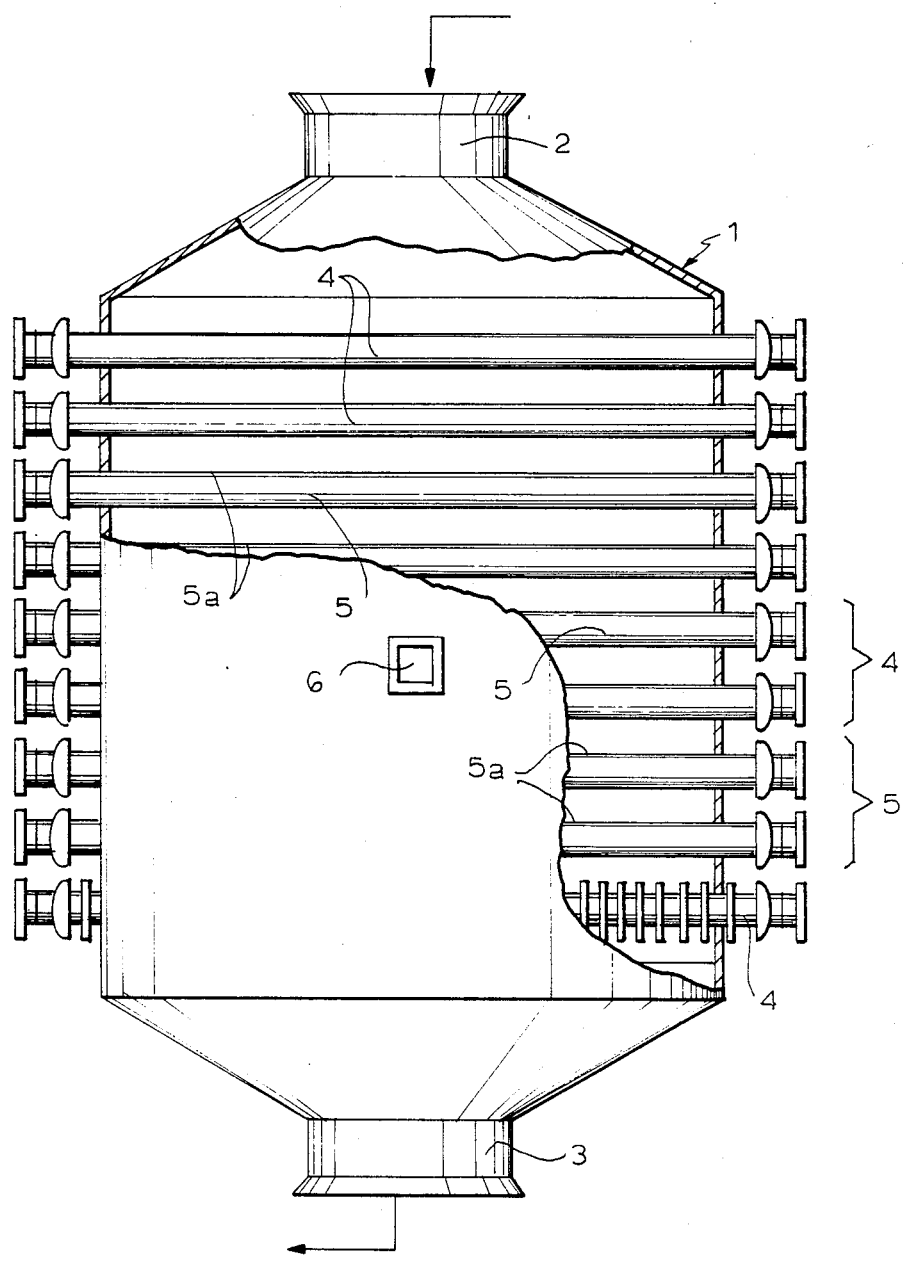

United States Patent [19]

Nikolov et al.

[11] Patent Number: 4,571,325
[45] Date of Patent: Feb. 18, 1986

[54] REACTOR FOR CONDUCTING HIGH EXOTHERMIC AND ENDOTHERMIC CATALYTIC PROCESSES

[75] Inventors: Valentin A. Nikolov, Ruse; Dimiter G. Klissurski, Sofia; Boyan M. Jurov, Ruse, all of Bulgaria

[73] Assignee: Stopanski chimitcheski Kombinat "Gavril Genov", Russe, Ruse, Bulgaria

[21] Appl. No.: 626,625

[22] Filed: Jul. 2, 1984

[30] Foreign Application Priority Data

Jul. 1, 1983 [BG] Bulgaria .................................. 61567

[51] Int. Cl.⁴ .......................... B01J 1/00; B01J 8/04; B01J 10/00; C10G 34/00
[52] U.S. Cl. .................................. 422/191; 422/201; 422/211; 422/311; 502/527
[58] Field of Search .............. 422/191, 197, 198, 200, 422/201, 312, 311, 241, 195, 211, 190, 297, 300; 502/527

[56] References Cited

U.S. PATENT DOCUMENTS

| | | | |
|---|---|---|---|
| 2,469,329 | 5/1949 | Crowley, Jr. | 422/200 |
| 2,596,299 | 5/1952 | Simpson | 422/200 |
| 2,778,610 | 1/1957 | Bruegger | 502/527 |
| 3,868,393 | 2/1975 | Reuter et al. | 562/408 |
| 3,927,997 | 12/1975 | Child et al. | 252/373 |
| 4,126,430 | 11/1978 | Roberge | 422/191 |
| 4,341,737 | 7/1982 | Albano et al. | 422/191 |
| 4,419,337 | 12/1983 | Jagodzinski et al. | 422/190 |
| 4,432,890 | 2/1984 | Beck et al. | 502/65 |

Primary Examiner—Barry S. Richman
Assistant Examiner—Titus B. Ledbetter, Jr.

[57] ABSTRACT

Reactor for conducting high exothermic and endothermic catalytic processes of partial oxidation, oxidizing ammonolysis, oxidizing dehydrogenation and so forth. The reactor has a shell in which there are disposed in sequence sets of tubes making up axially spaced heat exchange sections and contact sections alternating with each other, the tubes in the contact section being provided with catalysts deposited upon there outer surfaces. The shell is provided with an inlet port for raw material at the top thereof, a discharge port at the bottom thereof for removal of finished material, and at least one lateral port disposed between successive contact sections. The advantages of the reactor of the inventions lie in the quicker and easier method for deposition of catalysts upon the tubes within the contact sections, and in the lateral ports for feeding the reactor with raw material. As a result of this the temperature profile in the reactor is optimized and the productivity of the reactor is markedly increased.

6 Claims, 2 Drawing Figures

REACTOR FOR CONDUCTING HIGH EXOTHERMIC AND ENDOTHERMIC CATALYTIC PROCESSES

This invention relates to a reactor for conducting high exothermic and endothermic catalytic processes of partial oxidation, oxidizing ammonolysis, oxidizing dehyrogenation, etc., and more precisely, for conducting paraphasic oxidation of O-xylene and/or naphtalene to phthalic anhydride, benzol or $C_4$-hydrocarbons to maleic anhydride, durene to pyromellitic anhydride, etc.

A known reactor for conducting high exothermic and endothermic catalytic processes is disclosed in FRG (Federal Republic of Germany) Pat. No. 1,643,703 and FRG Pat. No. 2,820,454. Such known reactor comprising a shell in which there are placed tubes filled with catalyst in the form of granules, spheres, cylinders, etc., with heat carrier circulating in the area between the tubes. A disadvantage of this reactor is that the optimum temperature profile can be reached only in a narrow zone of the catalyst, and hot spots may appear, as a result of which the catalyst is quickly deactivated, and the production of the desired product decreases.

Another known reactor for conducting high exothermic catalytic processes is disclosed in FRG Pat. No. 2,118,871 and U.S. Pat. No. 3,868,393, Feb. 25, 1975, to Reuter et al. This known reactor comprises a shell in which there are placed tubes having a thin film of catalyst deposited on part of their inner surfaces with a fluid heating agent circulating in the area between the tubes. The shell has an input port to receive the raw material and an output port to discharge the finish product, as well as inlet and outlet ports for the fluid heating medium.

A disadvantage of the above-described known reactor is the very difficult deposition of the catalyst on the inner surface of the tubes because their internal diameter is only 15-20 mm, while their length is from 1500 to 7000 meters. To deposit two or more catalysts with different activities on the inner surface of the tubes is also very difficult. The raw material is supplied only from one entrance port of the reactor, and an additional feeding from another place is not possible. As a result of this, the possibility of the appearance of hot spots in the catalyst is not avoided, as well as the danger from operation with explosion-hazard concentrations.

The invention has among its objects the provision of a reactor for conducting high exothermic and endothermic catalytic processes in the reactor, the catalyst or catalysts can be easily deposited on the surfaces of supports such as tubes; a reactor of the invention also has the possibility of providing additional inlet ports to feed raw materials into the reactor, in order to avoid the appearance of hotspots and in order to conduct safer operations with explosion-hazard concentrations.

These objects and others are achieved by creating a reactor, for conducting high exothermic and endothermic catalytic processes, comprising a vertical shell in which there are disposed heating medium conducting tubes and supports for one or more catalysts; the shell is provided with a port for receiving raw materials and with a port for discharging the finish product. The heating medium conducting tubes are disposed in axially spaced planes perpendicular to the axis of the reactor and in the form of consecutively alternating groups of heat exchange sections and sections of support bearing the catalyst deposited on the outer surface of such supports. As above noted, the catalyst supports may take the form of tubes. The shell is provided with lateral ports, disposed vertically within contact sections. The heat exchange sections are disposed alternating with the contact sections, so that at least one heat exchange section is disposed between the consecutive contact sections. The catalyst in the different contact sections may be of one and the same, or of different compositions. The tubes of the contact and heat exchange sections may be smoothed or finned. The tubes of the contact and heat exchange sections are disposed in parallel regions comprising tubes which extend perpendicularly to and are axially spaced along the vertical axis of the shell, in a first disclosed embodiment all of the tubes being parallel, and in a second disclosed embodiment the tubes in the contact sections and those in the heat exchange sections being disposed in planes lying at substantial angles, such as 90°, with respect to each other.

The advantages of the reactor of the invention for conducting high exothermic and endothermic reactions are the following:

The deposition of the catalyst or catalysts on the outer surface of the catalyst supports such as tubes is easier and faster, and the catalysts coating are of good quality, so that the necessity for filling the tubes with catalyst or inert pellets, rings, cylinders etc., is eliminated; thus the weight of the reactor and its hydraulic resistance are considerably reduced. The means for feeding the raw materials from several places in the reactor, and the possibilities for changing the temperature in the separated contact sections within wide limits provide the possibility of an optimum temperature profile in the reactor and a considerable increase in the productivity of the catalytic process conducted therein.

Figure 2:
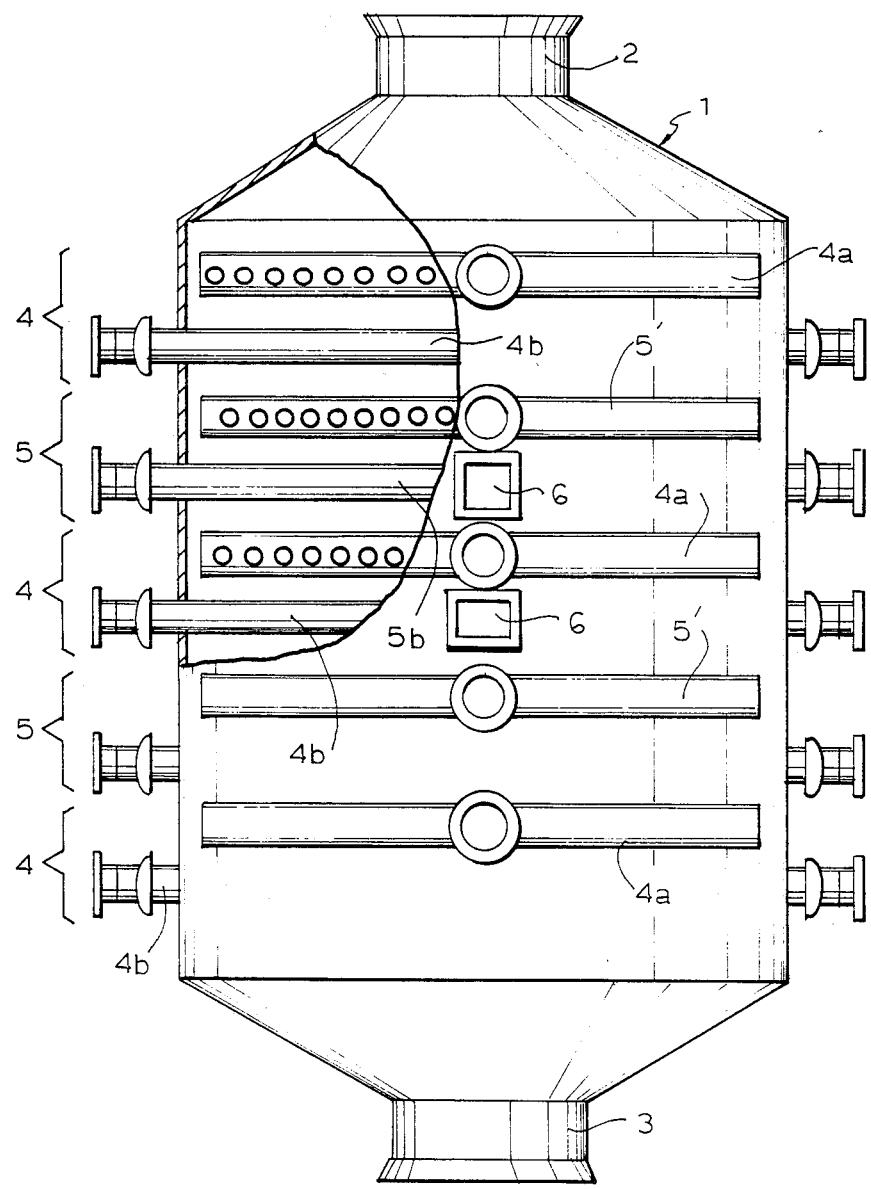

Preferred constructions of the reactor for conducting high exothermic and endothermic catalytic processes embodying the principles of the present invention are shown by way of example in the accompanying drawings, in which:

FIG. 1 is a view in longitudinal section through a first embodiment of the reactor; and FIG. 2 is a view in longitudinal section through a second embodiment of the reactor in which the catalytic bearing section are disposed at an angle with respect to the heat exchange section.

Turning first to FIG. 1, the reactor for conducting exothermic and endothermic catalytic processes thereshown comprises a shell 1 in which there are disposed a plurality of horizontal tubes disposed in two respective groups, the first group designated 4, being composed of first parallel horizontal sets of heat exchange tubes 4, and the second group being composed of two sets of contact tubes 5. It can be said that the groups of tube groups 4 alternate with the groups of tube groups 5, with the exception that only one set of heat exchange tubes 4 is employed at the bottom of the shell one. This, however, is not a limiting condition since instead of one set of heat exchange tubes 4 at the bottom of the shell 1 there may be employed two such sets, as at the top thereof.

Heat exchange fluid flows through the tubes 4 and 5, being fed there into from manifolds at the inlet ends of the tubes and being discharged therefrom into manifolds at the discharged ends of the tubes. The tubes of the set of tubes 5, that is the contact tubes, are provided with coatings 5a over all or portions of there outer surfaces. Raw material to be treated is introduced into shell 1 through the upper inlet port 2, and the reactor of products are led from the shell 1 through a bottom port 3. The shell 1 is provided with one or more lateral ports 6 for feeding other or additional raw material into the shell.

The reactor illustrated in FIG. 1 and above described operates as follows:

Raw materials supplied through the upper port 2 and through the lateral nipple or nipples 6, are passed through the heat exchange sections made up of the group of tubes 4, and after being heated up to the desired temperature of the material being treated is passed to the contact sections made up of the groups of tubes 5, where the catalytic reaction takes place. The optimum temperature of the reactors is kept up by means of the heat exchange medium, which flows through the tubes in the heat exchange sections 4 as well as through the tubes in the contact sections 5. The raw materials being treated, after once being heated, also tends to maintain the desired temperature within the shell 1. After passing through the contact sections 5, the reaction products are cooled to the necessary temperature by passing them through lower heat exchange sections 5 which may be temperature controlled independently of the upper heat exchange sections, and then the finally treated material is discharged from the shell through the outlet port 3.

FIG. 2 shows a second illustrative embodiment of the reactor of the invention, such reactor having the tubes forming the heat exchange sections and the contact sections each made up of a first set of tubes which is disposed horizontally and extending in a first direction and a second set of tubes which lies horizontally and extends in a direction at right angles to the first set of tubes.

In FIG. 2 the reactor has a shell 1. Within the shell there are disposed a heat exchange group of tubes 4 at the top, following which there is disposed a contact section 5 followed and turned by a heat exchange section 4, then contact section 5 finally a heat exchange section 4, disposed near the bottom of the shell. As in the case of the first described reactor of FIG. 1, the shell 1 has an inlet port 22 at the top for receiving raw material, and a discharge port 3 at the bottom for discharging treated material. The shell also has a plurality of lateral ports 6, of which two are shown, disposed at an intermediate height of the shell for receiving more of the same material or possibly different material to be mixed with the initial material and to be treated therewith in the lower portions or portion of the reactor. Each of the heat exchange sections 4 is made up of a set 4a of tubes extending in a different direction perpendicular to the plane of the paper of the drawing, and a further section 4b disposed horizontally and spaced laterally in a direction parallel to the plane of the paper. Each of the contact sections 5 includes a first set of tubes in a section 5', the tubes therein extending perpendicularly to the plane of the paper, and a second set of tubes 5b extending horizontally and parallel to each other in directions parallel to the plane of the paper.

As in the embodiment of FIG. 1, heat exchange fluid is circulated through the tubes of each of sets 4 and 5. Also as in the embodiment of FIG. 1, the heat exchange medium in the various sets of tubes may be individually controlled. The catalyst in the different contact sections 5, may be of one and the same or or different composition. The tubes of the contact sections 5 and heat exchange section 4 can be finned or smooth.

Although the invention is described and illustrated with reference to a plurality of embodiments thereof, it is to be expressly understood that it is in no way limited to the disclosure of such preferred embodiment but is capable of numerous modifications within the scope of the appended claims.

We claim:

1. A reactor for conducting highly exothermic and endothermic catalytic processes, said reactor comprising a vertical shell provided with an upper inlet port for receiving raw materials and a lower outlet port for discharging product therefrom, a plurality of regions therein which extend peripendicular to, and are axially spaced along, the vertical axis of said shell, each said region being formed of a plurality of tube means, said regions constituting alternating contact regions and heat exchange regions with adjacent contact regions being separated by a heat exchange region, each tube means of a contact region being coated on the outer surface thereof with a catalyst and each tube means of a heat-exchange region being devoid of such a catalyst coating, means operatively connected to all of said tube means for providing flow a heat-exchange medium therethrough and said shell being provided with at least one lateral port disposed between each pair of adjacent contact regions.

2. A reactor according to claim 1, wherein said catalyst deposited on the outer surfaces of the tube means of each of the contact regions is the same composition.

3. A reactor according to claim 1, wherein a plurality of catalyst coatings are deposited on the outer surfaces of the tube means, each of said catalysts being deposited on the tube means of one of the contact regions.

4. A reactor according to claim 1, wherein the tube means of the contact regions and of the heat exchange regions are smooth.

5. A reactor according to claim 1, wherein the tube means of the contact regions and of the heat exchange regions are finned.

6. A reactor according to claim 1, wherein the tube means making up the heat exchange regions are made up of sets of tube means disposed at marked angles with respect to each other, and the tube means making up the contact regions are made up of sets of tube means disposed at marked angles with respect to each other.

* * * * *